(12) United States Patent
Kordonski et al.

(10) Patent No.: US 7,557,566 B2
(45) Date of Patent: Jul. 7, 2009

(54) METHOD AND APPARATUS FOR MEASUREMENT OF MAGNETIC PERMEABILITY OF A MATERIAL

(75) Inventors: William Kordonski, Webster, NY (US);
Arpad Sekeres, Rochester, NY (US);
Robert James, Rochester, NY (US)

(73) Assignee: QED Technologies International, Inc., Aurora, IL (US)

( * ) Notice: Subject to any disclaimer, the term of this patent is extended or adjusted under 35 U.S.C. 154(b) by 99 days.

(21) Appl. No.: 11/681,258

(22) Filed: Mar. 2, 2007

(65) Prior Publication Data
US 2008/0214092 A1 Sep. 4, 2008

(51) Int. Cl.
*G01N 27/74* (2006.01)
*G01B 7/00* (2006.01)

(52) U.S. Cl. ...................... 324/204; 324/239

(58) Field of Classification Search ................. 324/204, 324/207.15–207.19, 228, 232, 234, 239–240, 324/256–263; 188/267, 267.2
See application file for complete search history.

(56) References Cited

U.S. PATENT DOCUMENTS

| | | | |
|---|---|---|---|
| 2,790,950 A | * | 4/1957 | Miller .................. 324/227 |
| RE34,039 E | * | 8/1992 | Kobayashi et al. ..... 73/862.336 |
| 5,554,932 A | | 9/1996 | Jeffers |
| 5,971,835 A | | 10/1999 | Kordonski |
| 6,650,108 B2 | | 11/2003 | Carlson |
| 6,746,310 B2 | | 6/2004 | Tricard |
| 6,893,322 B2 | | 5/2005 | Kordonski |
| 2003/0020463 A1 | * | 1/2003 | Carlson et al. .............. 324/204 |

* cited by examiner

*Primary Examiner*—Bot LeDynh
(74) *Attorney, Agent, or Firm*—Thomas Omholt; Robert C. Brown; Steven Weseman

(57) ABSTRACT

A system for determining the magnetic permeability of a material is provided. Two electrical inductors formed as primary and secondary concentric coils share a common magnetic core space. An AC voltage applied to the primary coil creates a magnetic flux in the core proportional to the magnetic permeability of a sample of the material positioned within the core space. The magnetic flux induces an AC voltage in the secondary coil indicative of the sample magnetic permeability. When the material is a magnetorheological fluid, the magnetic permeability is proportional to the concentration of magnetic particles in the sample and can be back-calculated from the amplitude of the secondary voltage signal. Sensitivity and resolution can be increased by using two identical sets of coils wherein a reference material forms a core for the primary set and the MR fluid sample forms a core for the secondary set.

5 Claims, 4 Drawing Sheets

METHOD AND APPARATUS FOR MEASUREMENT OF MAGNETIC PERMEABILITY OF A MATERIAL

BACKGROUND OF THE INVENTION

1. Field of the Invention

The present invention relates to methods and apparatus for inferential measurement; more particularly, to methods and apparatus for determining the magnetic permeability of a material; and most particularly, to a method and apparatus for using such measurement to control the concentration of a magnetic material in a magnetorheological (MR) fluid.

2. Discussion of the Related Art

MR fluids are well known and may be defined practically as fluid materials whose apparent viscosities are reversibly increased by exposure of the fluid to a magnetic field. The increase in viscosity is anisotropic, being greatest in the direction of the magnetic field due to formation of fibrils of magnetized particles. This property, known in the art as "stiffening", has been employed to great success in the field of extremely high resolution shaping, finishing, and polishing of surfaces, especially optical elements, wherein very small amounts of material may be removed in a highly precise and controlled manner. This field is known generally in the art as magnetorheological finishing (MRF). See, for example. U.S. Pat. Nos. 5,971,835; 6,746,310; and 6,893,322, the relevant disclosures of which are incorporated herein by reference.

A problem in the art of MRF is maintaining a constant magnetic particle concentration in the MR fluid entering the magnetic work zone. MR fluid is supplied to the work zone by a delivery system that draws MR fluid from a mixing sump into which used MR fluid passes from the work zone for mixing and reuse. The used MR fluid typically is depleted in carrier (water) by evaporation and also is heated, both of which alterations must be corrected before the MR fluid may be reused. Without replenishment of water lost to evaporation, the bulk supply of MR fluid in the sump will gradually increase in particle concentration during an MRF operation. This is an undesirable operating condition because particle concentration is an important factor governing the rate of removal of material from a substrate being finished. Thus, it is important to know what the particle concentration is in the MR fluid being supplied from the sump at any given time and to provide a proper water replenishment rate to the sump to replace the water lost to evaporation in use, thereby dynamically keeping the concentration constant at an aim value.

U.S. Pat. No. 5,554,932 discloses a system for measuring magnetic saturation flux density of a sample material. First and second sample holders are disposed symmetrically on either side of a cylindrical permanent magnet. Coils are placed around the sample holders and the permanent magnet is rotated. The signals induced in the coils in the absence of a magnetic material in one of the sample holders are applied to an amplifier/meter in such a manner as to provide a null signal. When a sample is placed in one of the sample holders, the magnetic saturation flux density can be measured. A shortcoming of the disclosed system is that the mechanical device is relatively cumbersome and has a critical moving part (the permanent magnet).

U.S. Pat. No. 6,650,108 discloses a system for inferring concentration of magnetic particles in a flowing MR fluid. The system is based on inductance measurement that converges in an impedance measurement with relatively complex technique involving high sensitivity electric bridge circuits. A shortcoming of the disclosed system is that resolution is relatively low.

What is needed in the art is a simple, high-resolution means for continuously measuring and monitoring the concentration of magnetic particles in the mixed sump MR fluid to permit controlled real-time dilution thereof before the sump MR fluid is reused for finishing.

It is a principal object of the present invention to assist in providing an MR fluid of constant particle concentration to an MRF work zone.

SUMMARY OF THE INVENTION

Briefly described, in a method and apparatus of the present invention, two electrical inductors share the same magnetic core. Preferably, the inductors are formed as primary and secondary concentric coils. When an AC voltage is applied to the primary coil, an axially-directed magnetic flux is created in the core which is proportional in intensity to the magnetic permeability of the core. In turn, due to the effect of mutual inductance, the magnetic flux induces an AC voltage in the secondary coil which is in phase with the source voltage. The magnetic permeability of the core depends upon the concentration of magnetic particles in the sample (when the "core" is a sample of MR fluid), and thus the concentration of magnetic particles can be back-calculated from the amplitude of the secondary voltage signal.

Sensitivity of measurements and system resolution can be increased by using a differential approach using two identical sets or pairs of coils wherein a reference material forms a magnetic core for one coil set and the MR fluid forms a magnetic core for the other coil set.

BRIEF DESCRIPTION OF THE DRAWINGS

The foregoing and other objects, feature, and advantages of the invention, as well as presently preferred embodiments thereof, will become more apparent from a reading of the following description in connection with the accompanying drawings in which.

DETAILED DESCRIPTION OF THE INVENTION

Figure 1:
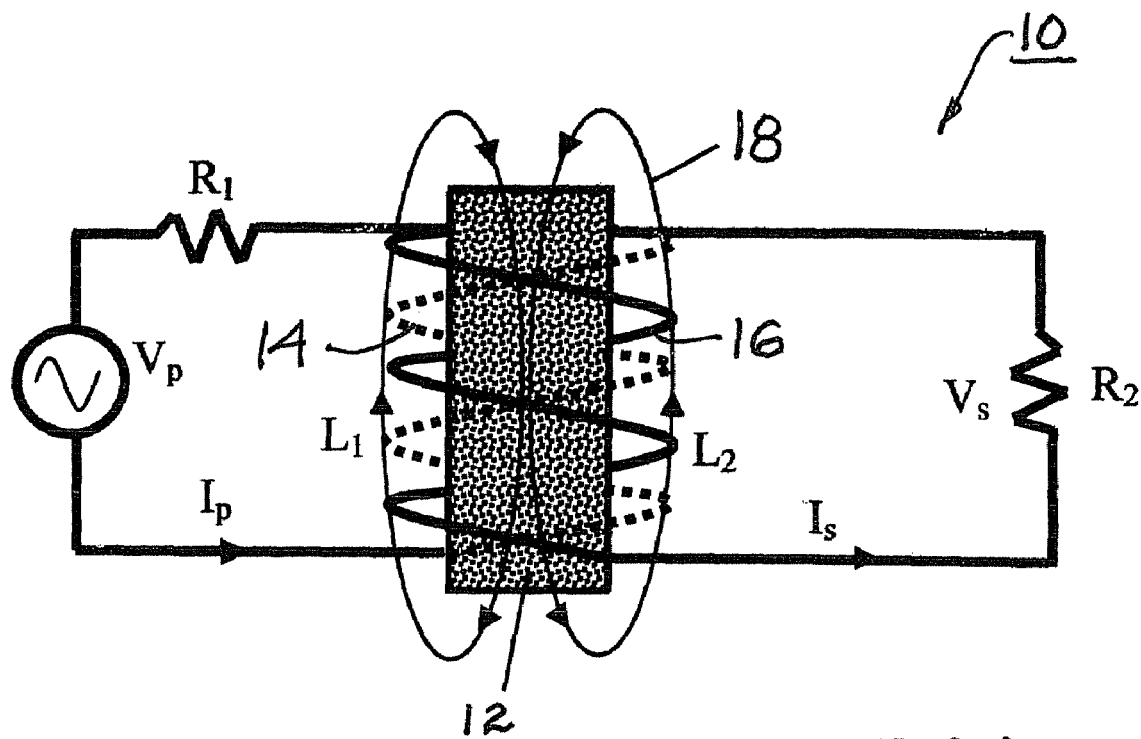
FIG. 1 is a schematic drawings of a first embodiment of a system in accordance with the invention for measuring magnetic permeability.

Referring to FIG. 1, in a system 10 in accordance with the invention suitable for measuring the magnetic permeability of the material of a magnetic core 12, two inductors (primary coil 14 and secondary coil 16) share magnetic core 12, which is a sample of a magnetic material, such as MR fluid, to be tested. When an AC voltage $V_p$ is applied to primary coil 14, an axially-directed magnetic flux 18 is created in core 12 in accordance with Equation 1:

$$B = \mu \frac{N}{l} \frac{I_p}{\sqrt{2}} \quad \text{(Eq. 1)}$$

where μ is the magnetic permeability of the core, N is the number of primary coil turns, l is the coil's length, $I_p$ is the current amplitude, and $I_p/\sqrt{2}$ is the root mean square current.

In turn, due to the effect of mutual inductance, magnetic flux 18 induces and AC voltage $V_s$ in secondary coil 16 in phase with the source voltage in accordance with Equation 2:

$$V_s = 2\pi f N A B \quad \text{(Eq. 2)}$$

where f is current frequency and A is the cross-sectional area of core 12. From Equation 1 and Equation 2, it follows that the root mean square voltage $V_s$ generated in secondary coil 16 is given by Equation 3:

$$V_s = 4.44 \, \mu f \frac{N^2 A}{l} I_p \quad \text{(Eq. 3)}$$

Primary coil 14 behaves as a load with respect to the AC voltage source $V_p$, and secondary coil 16 behaves as a source with respect to resistor $R_2$. At the same time, the magnetic permeability μ depends on magnetic properties of core 12. In turn, these properties are dependent on concentration of the magnetic particles φ in the sample, as given by Equation 4:

$$\mu = f(\varphi) \quad \text{(Eq. 4)}$$

When all parameters of system 10, including the AC voltage applied to the primary coil, are held constant, any variation in concentration of magnetic particles in core 12 will result in a proportional change of AC voltage $V_s$ in secondary coil 16. In doing so, the system output signal follows variations in the sample magnetic particles concentration. In the general case, it can be defined as shown in Equation 5:

$$V_s = f(\varphi, k_1, k_2 \ldots) \quad \text{(Eq. 5)}$$

where $k_1, k_2 \ldots$ are some constant parameters which depend on system geometry and system electrical parameters. The magnitude of output signal can be manipulated by (pre) setting the different system parameters such as number of turns and geometries of the coils, frequency and voltage of the oscillator, impedance of the components, and the like. System 10 further may contain a temperature sensor (not shown), such as a thermistor, and means to compensate for thermal variation in circuit impedance and change in output signal due to variations of temperature.

A quantitative relationship between the concentration and the voltage $V_s$ in secondary coil 16 is determined by calibration with samples of known magnetic particles concentration. The calibration gives the general expression for concentration according to Equation 6:

$$\varphi = a V_s + b \quad \text{(Eq. 6)}$$

where a and b are constants defined by calibration.

Figure 2:
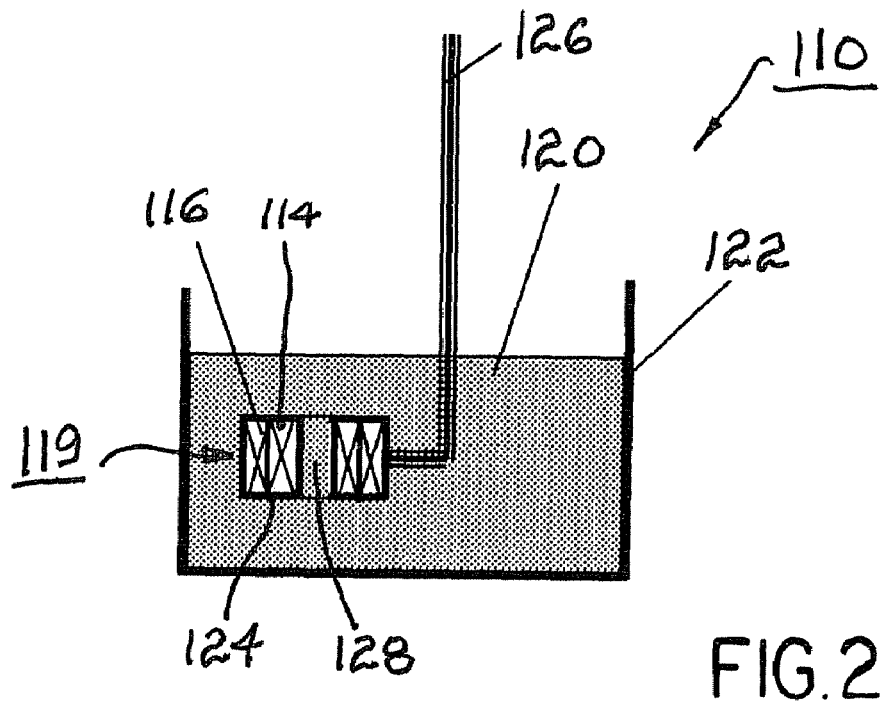
FIG. 2 is a schematic drawings showing the first embodiment in use in an MR fluid.

Referring to FIG. 2, in an exemplary embodiment 110 for measuring magnetic permeability of an MR fluid 120 is a vessel 122, primary and secondary coils 114, 116 of a double-coil sensor unit 119 are encapsulated in a waterproof case 124 material and a wand 126 carrying electrical leads (not shown) is provided to submerge the coils in MR fluid 120 which fills sample cell 128 within the coils, thereby defining the magnetic core of the system. Measurement is then made as described below.

Figure 3:
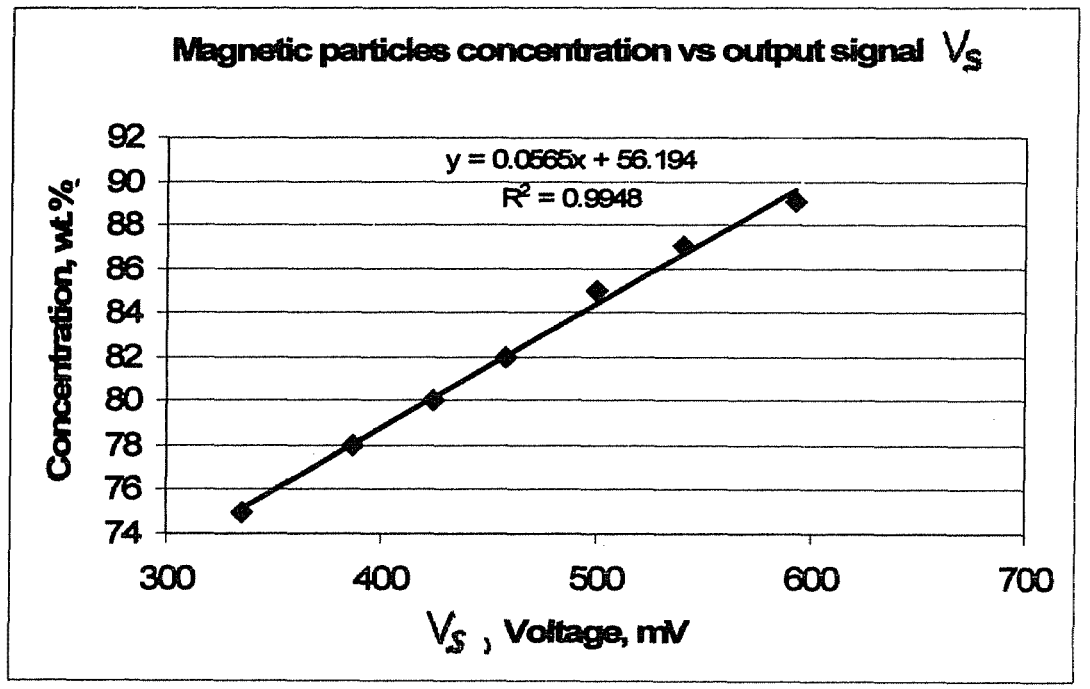
FIG. 3 is a calibration curve for the first embodiment showing the relationship between output voltage and concentration of magnetic particles in an MR fluid.
Figure 4:
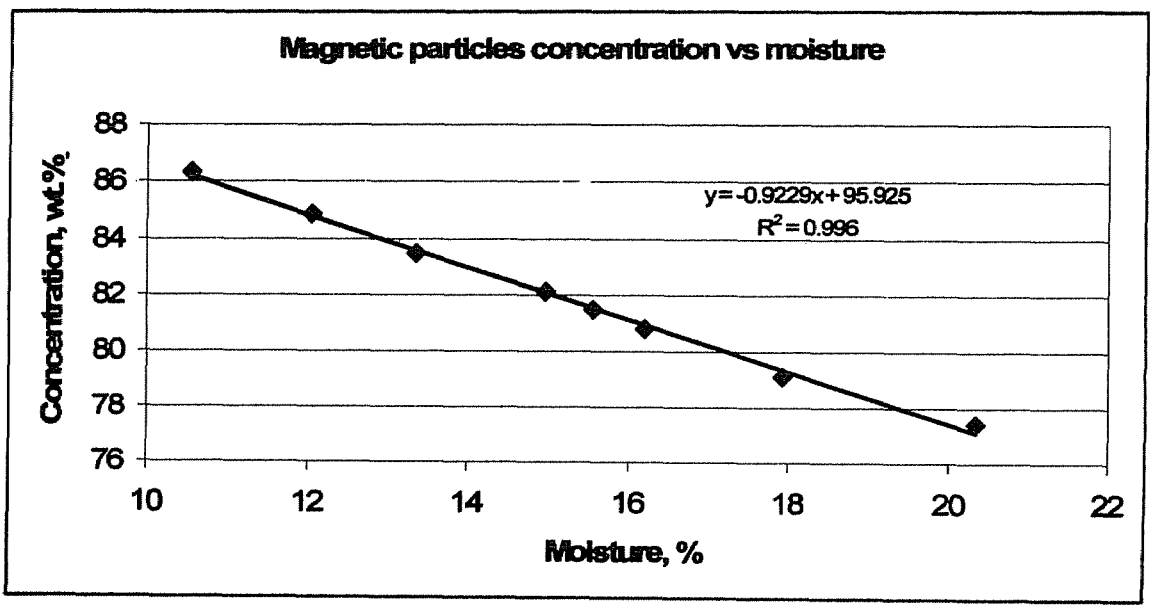
FIG. 4 is a calibration curve for the first embodiment showing the relationship between moisture percentage and concentration of magnetic particles in an MR fluid.

Referring to FIGS. 3 and 4, samples of water-based MR fluid were used for testing and system calibration. In the present example, each coil had 200 turns, and the AC frequency of primary voltage $V_p$ was 1000 Hz. Moisture (amount of water), which defines the concentration of magnetic particles, was measured with Moisture Analyzer HB43, available from Mettler-Toledo Gmbh, Switzerland. FIGS. 3 and 4 show an excellent linear dependence of concentration on voltage and moisture, respectively, in the range of measured concentrations, as predicted by Equation 6.

Figure 5:
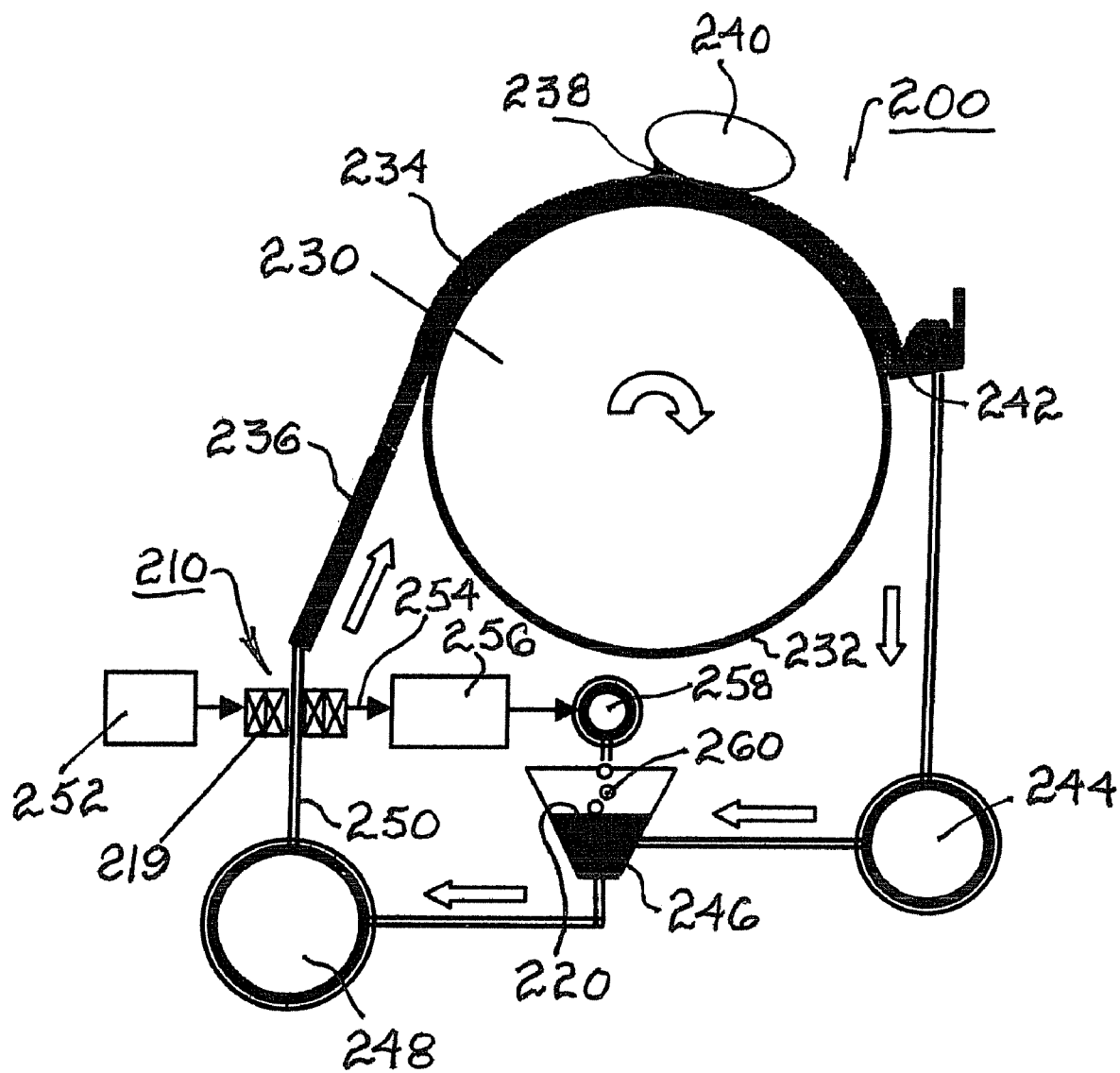
FIG. 5 is a schematic drawing showing application of the first embodiment to an MRF system.

Referring to FIG. 5, an exemplary application is shown for a system 210 in accordance with the present invention in assisting in maintaining a constant concentration of magnetic particles in MR fluid in an MR finishing apparatus 200.

As is known in the prior art for an MR finishing apparatus 200 and described more fully in the incorporated references, a carrier wheel 230 has a surface 232, preferably spherical, for receiving a ribbon 234 of MR fluid in a non-stiffened state from nozzle 236. Surface 232 and an off-spaced work piece 240 to be finished. Shaped magnetic pole pieces (not shown) create an orientated magnetic field within work zone 238 that causes the MR fluid therein to become stiffened to a consistency approximating putty. The stiffened MR fluid, which may also contain non-magnetic particles of abrasives such as cerium oxide, ablates the surface of work piece 240 in controlled fashion as it is drawn through work zone 238. Carrier surface 232 continuously supplies and removed MR fluid to and from work zone 239. A scraper 242 removed used MR fluid, no longer stiffened, from carrier surface 232 and returned it via a suction pump 244 to a mixing sump 246, wherein the used MR fluid is mixed with a bulk supply of MR fluid 220 and from whence mixed MR fluid 220 is drawn by delivery pump 248 and supplied again to nozzle 236 via non-magnetic tube 250.

A double-coil mutual inductance sensor 219 in accordance with the present invention and controllably driven by an AC power supply 252 as described above is placed concentrically outside non-magnetic tube 250 filled with flowing MR fluid 220. Sensor 219 provides in-line measurement/monitoring of concentration of magnetic particles in MR fluid 220 flowing through the sensor. An output signal 254 is directed to a programmable controller 256, programmed in accordance with FIGS. 3 and 4 and having a set point corresponding to an aim concentration, which controls a pump 258 to dispense replenishment water 260 into sump 246 at a controlled flow rate to compensate for water evaporated from the MR fluid ribbon 234 when exposed on carrier wheel 230 during use thereof. Replenishment water 260 is mixed with the bulk supply MR fluid within sump 246 to dilute the bulk concentration to aim. Thus, the concentration of magnetic particles in MR fluid 220 as drawn from sump 246 for supply to work zone 238 is maintained at the aim concentration, providing a stable and predictable rate of material removal from work pieces 240.

Figure 6:
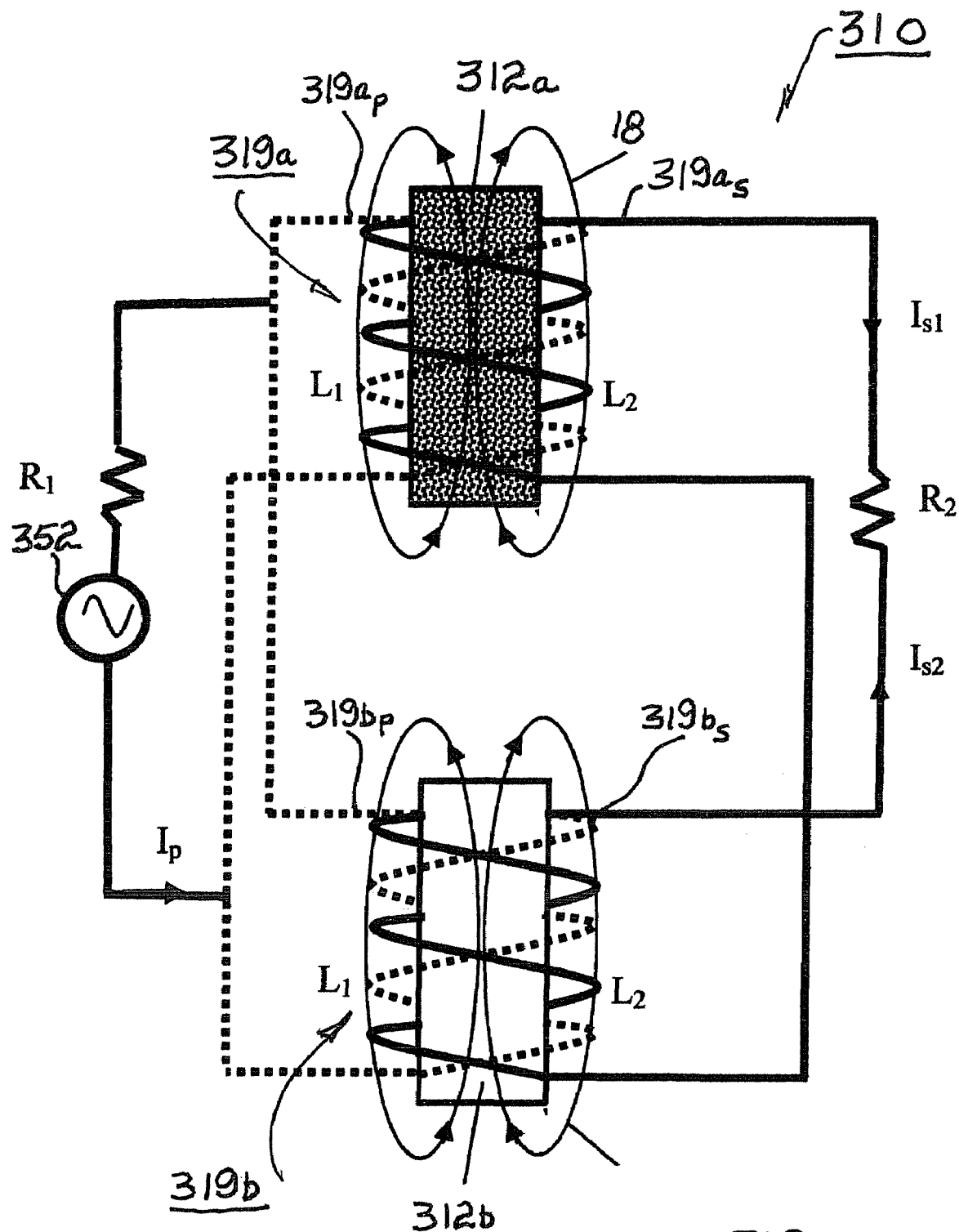
FIG. 6 is a schematic drawing of a second embodiment of a system in accordance with the invention.

Referring now to FIG. 6, in a second embodiment 310 of an inductance coil system in accordance with the invention, sensitivity of measurements and system resolution can be increased using a differential approach/methodic. In embodiment 310, two identical sets 319a and 319b of coil pairs are used. First coil set 319a surrounds a magnetic core sample 312a to be tested, and coil set 319b surrounds a core sample 312b of a reference material with known magnetic permeability, for example, air. (Obviously, the designation of first and second coil sets is arbitrary, as the sets are identical; either one may be the sample set, the other the reference set.) Both primary coils $319a_p$, and $319b_p$ are connected to AC voltage source (oscillator) 352 in parallel. Secondary coils $319a_s$, $319b_s$ are connected in series but are wired so that currents $Is_1$, $Is_2$ of the secondary coils are oppositely directed through resistance $R_2$; thus, the resulting current will be equal to zero when the same samples or no samples are placed inside the coils. System 300 obviously may contain some additional common means (not shown) to accurately balance the system when, for example, sample 312a is an MR fluid of the correct magnetic permeability. Any system misbalance caused by the change in magnetic properties of sample 312a (assuming reference sample 312b is held constant) results in a proportional output signal, analogous to signal 254 in FIG. 5. At the same time, any changes in impedance of the circuits cased by the temperature will not affect the output signal because such changes occur in both the sample and reference circuits and thus they cancel each other.

While second embodiment 310 shows improved sensitivity and resolution over the first embodiment 210, implementation thereof can be somewhat more complex and expensive; ergo, first embodiment 210 may be a satisfactory choice for MRF applications.

While the invention has been described by reference to various specific embodiments, it should be understood that numerous changes may be made within the spirit and scope of the inventive concepts described. Accordingly, it is intended that the invention not be limited to the described embodiments, but will have full scope defined by the language of the following claims.

What is claimed is:

1. A system for determining magnetic permeability of a material, comprising:
   a) a first electrical inductor;
   b) a second electrical inductor;
   c) an AC voltage source connected to said first electrical inductor to induce a magnetic field surrounding said first and second electrical inductors and a sample of said material; and
   d) means for measuring an induced AC voltage in said second electrical inductor, wherein the amplitude of said induced AC voltage is proportional to said magnetic permeability of said material,
   wherein said first electrical inductor is a first coil, said second electrical conductor is a second coil coaxial with said first coil, said magnetic field is axially-directed within said first and second coils, and said sample of said material is disposed within said axially-directed magnetic field, and
   wherein said first and second coils define a sample cell having a first sample coil and a second sample coil for receiving a test sample of said material, said system further comprising
   a reference cell having a first reference coil and a second reference coil for receiving a sample of a reference material having known magnetic permeability;
   means connecting said first sample coil and said first reference coil in parallel to said AC voltage source;
   means connecting said second sample coil and said second reference coil in series wherein a sample current induced in said second sample coil is opposed by a reference current induced in said second reference coil; and
   means for determining a difference in amplitude between said sample current and said reference current, said difference being proportional to said magnetic permeability of said test sample relative to said magnetic permeability of said reference material.

2. A system in accordance with claim 1 wherein said second coil is wrapped around said first coil.

3. A system in accordance with claim 1 wherein said material is a magnetorheological fluid comprising magnetic particles dispersed in a liquid carrier and wherein said magnetic permeability is proportional to the concentration of magnetic particles in said liquid carrier.

4. A system in accordance with claim 1 wherein said system is a component of a magnetorheological finishing system.

5. A system in accordance with claim 4 wherein said magnetorheological finishing system comprises:
   a) a sump for storage of a bulk supply of magnetorheological fluid to supply and receive magnetorheological fluid during recirculating use thereof in said system, wherein said magnetorheological fluid comprises magnetic particles dispersed in a carrier fluid, and wherein the concentration of said particles in said carrier fluid is increased during said recirculating use by evaporative loss of a portion of said carrier fluid;
   b) a double-coil mutual inductance sensor including a primary coil and a secondary coil coaxially wound, defining a sample space within said primary and secondary coils for receiving a sample of said magnetorheological fluid from said bulk supply;
   c) means for imposing an AC voltage on said primary coil;
   d) means for sending a signal from said secondary coil representing amplitude of an AC voltage induced therein, said signal being proportional to the concentration of said magnetic particles in said carrier fluid in said sample;
   e) controller means responsive to said signal and having programmed means for comparing said signal to a stored reference signal indicative of an aim concentration of said magnetic particles dispersed in said carrier fluid and for calculating a flow rate of replenishment carrier fluid required for addition to said sump to replace said evaporative loss and thereby maintain said bulk supply of said magnetorheological fluid at said aim concentration; and
   f) dispensing means responsive to said controller means for dispensing said replenishment carrier fluid into said bulk supply at said calculated flow rate.

* * * * *